United States Patent
Alessandri (10) Patent No.: US 10,130,845 B2
(45) Date of Patent: Nov. 20, 2018

(54) GYMNASTIC MACHINE, SYSTEM, METHOD, AND PROGRAM PRODUCT FOR EASILY CONTROLLING THE TRAINING OF A USER ON A GYMNASTIC MACHINE

(71) Applicant: TECHNOGYM S.p.A., Cesena (IT)

(72) Inventor: Nerio Alessandri, Cesena (IT)

(73) Assignee: TECHNOGYM S.P.A., Cesena (IT)

( * ) Notice: Subject to any disclaimer, the term of this patent is extended or adjusted under 35 U.S.C. 154(b) by 73 days.

(21) Appl. No.: 15/116,318

(22) PCT Filed: Feb. 18, 2014

(86) PCT No.: PCT/IT2014/000041
§ 371 (c)(1),
(2) Date: Aug. 3, 2016

(87) PCT Pub. No.: WO2015/125162
PCT Pub. Date: Aug. 27, 2015

(65) Prior Publication Data
US 2017/0007886 A1    Jan. 12, 2017

(51) Int. Cl.
*A63B 24/00* (2006.01)
*G06F 19/00* (2018.01)
(Continued)

(52) U.S. Cl.
CPC .......... *A63B 24/0087* (2013.01); *A63B 21/06* (2013.01); *A63B 22/025* (2015.10);
(Continued)

(58) Field of Classification Search
CPC ............ A63B 24/0087; A63B 24/0062; A63B 24/0075; A63B 22/025; A63B 22/06;
(Continued)

(56) References Cited

U.S. PATENT DOCUMENTS

| | | | |
|---|---|---|---|
| 6,997,852 B2 * | 2/2006 | Watterson | A63B 22/02 482/1 |
| 9,578,185 B2 * | 2/2017 | Jung | H04N 1/00106 |

(Continued)

FOREIGN PATENT DOCUMENTS

| | | |
|---|---|---|
| CN | 101912676 A | 12/2010 |
| WO | 2013080108 A2 | 6/2013 |

OTHER PUBLICATIONS

Kevin C. Tofel: CES Preview Technogym's Google Glass Controlled Treadmill—Tech News and Analysis, Jan. 3, 2014, Retrieved from the Internet.

(Continued)

*Primary Examiner* — Glenn Richman
(74) *Attorney, Agent, or Firm* — Arent Fox LLP; Michael Fainberg (57) ABSTRACT

Gymnastic machine usable by a user for a training, said user being provided with an electronic device wearable by the user and configured to receive commands by the user.
The gymnastic machine comprises a main control unit configured to:
  receive from said electronic device, via a wireless-type data communication channel, an input command provided by the user to the electronic device;
  generate, based on the received input command, an operative command of the gymnastic machine;
  control the gymnastic machine based on said generated operative command.
A system, a method, and a corresponding program product for the simplified control of the training of a user on a gymnastic machine are also described.

22 Claims, 4 Drawing Sheets

(51) Int. Cl.
    *G09B 19/00*     (2006.01)
    *A63B 22/02*     (2006.01)
    *A63B 21/06*     (2006.01)
    *A63B 22/06*     (2006.01)
    *A63B 71/06*     (2006.01)
    *G05B 19/409*     (2006.01)

(52) U.S. Cl.
    CPC .......... *A63B 22/06* (2013.01); *A63B 24/0062* (2013.01); *A63B 24/0075* (2013.01); *A63B 71/0622* (2013.01); *G05B 19/409* (2013.01); *G06F 19/3481* (2013.01); *G09B 19/0038* (2013.01); *A63B 2024/0093* (2013.01); *A63B 2220/12* (2013.01); *A63B 2220/18* (2013.01); *A63B 2225/15* (2013.01); *A63B 2225/50* (2013.01); *A63B 2230/062* (2013.01); *G05B 2219/15117* (2013.01)

(58) Field of Classification Search
    CPC .......... A63B 2230/062; A63B 2225/50; A63B 2225/15; A63B 2220/18; A63B 2220/12; A63B 2024/0093; A63B 71/0622; A63B 21/06; G06F 19/3481; G09F 19/0038; G05B 19/409; G05B 2219/15117
    See application file for complete search history.

(56) References Cited

U.S. PATENT DOCUMENTS

| | | |
|---|---|---|
| 2002/0022551 A1 | 2/2002 | Watterson |
| 2016/0224036 A1* | 8/2016 | Baker ................ G05D 23/1393 |
| 2017/0007886 A1* | 1/2017 | Alessandri .......... G06F 19/3481 |
| 2017/0277508 A1* | 9/2017 | Carthen .................. G06F 3/014 |

OTHER PUBLICATIONS

International Search Report and Written Opinion for PCT/IT2014/000041 dated Sep. 29, 2014.

\* cited by examiner

GYMNASTIC MACHINE, SYSTEM, METHOD, AND PROGRAM PRODUCT FOR EASILY CONTROLLING THE TRAINING OF A USER ON A GYMNASTIC MACHINE

FIELD OF THE TECHNOLOGY

The present invention relates to the field of fitness, and particularly to a gymnastic machine, a system, a method, and a corresponding program product for easily controlling the training of a user on a gymnastic machine.

BACKGROUND

The training of a user on a gymnastic machine was typically followed almost only by specialized personnel (personal trainers) of the gym.

Technological evolution of gymnastic machines led to decrease the direct assistance by a personal trainer.

For example, the instructions for using and/or configuring a gymnastic machine before a training may be used by the user through a display with which the control panel of the gymnastic machine is provided. Subsequently, the user proceeds autonomously to configure the gymnastic machine through the commands with which the above-mentioned control panel is provided.

However, despite these simplifications, the configuration and, generally, the control of the gymnastic machine before and while performing a training seem still quite complex, especially for people who do not have a particular familiarity with technology, for example, the elderly, or generally people who are less familiar with fitness.

In fact, the use of a control panel, even a touch-screen one, in which, for example, due to reasons of amount of space, the icons are displayed small, or writings are indicated with abbreviations or in a language that is different from the user's one could be not so intuitive.

Furthermore, while performing the training (for example, a run on a treadmill), the interaction of the user with a control panel may involve an abnormal movement of the body, such as to change the proper, ideal posture of the user during the training, which could thus turn out to be performed not in optimal conditions.

Furthermore, as regards the data or parameters of the training being carried out that may be displayed on the display of the control panel (for example, the speed or slope in the case of a run, walk or pedal), a user under a strain could not be capable of reading immediately or correctly such data, both due to his/her fatigue, and due to the poor visibility of such digits, for example, in the case of a gymnastic machine with a very small display.

In a gymnastic machine without a display, such data may be used by the user even only at the end of the training (for example, by accessing a computer connected to the gymnastic machine). However, it is certainly very important to know such data while performing the training, so as to be able to know whether the physical exercise is being performed correctly or not.

Again, in such a kind of gymnastic machine (without a display or a control panel), the user has the drawback of having to interface first with a computer (connected to the gymnastic machine) to set the training parameters.

Therefore, it is strongly and continuously felt the need to have gymnastic machines, or more generally systems for controlling such gymnastic machines that are more and more capable of simplifying the autonomous use of such gymnastic machines even by more or less skilled users both from the technological and fitness point of view.

SUMMARY

The object of the present invention is to provide a gymnastic machine, the control of which during the training by a user is more simplified, allowing obviating the drawbacks set forth herein above with reference to the prior art.

Such an object is achieved by a gymnastic machine in accordance with claim 1.

Also a system, a method, and a corresponding program product for the simplified control of the training of a user on a gymnastic machine are the object of the present invention.

BRIEF DESCRIPTION OF THE DRAWINGS

Further characteristics and advantages of the gymnastic machine, the system, the method, and the program product according to the invention will be apparent from the description set forth below of preferred implementation examples, given by way of indicative, non-limiting example, with reference to the appended Figures, in which.

DETAILED DESCRIPTION

It is pointed out that in the Figures, like or similar elements will be indicated with the same numeric or alphanumeric references.

With reference to the FIGS. 1 and 2, a system 100 for controlling the training of a user, herein below simply referred to as the system, according to an embodiment of the invention, will be now described.

The system 100 comprises an electronic device 1 wearable by the user, herein below also the electronic device 1 of the user or, simply, electronic device 1, while performing the training.

The electronic device 1 wearable by the user is advantageously configured to receive commands of the gymnastic machine 2 from the user. Examples of commands of the gymnastic machine 2 will be indicated herein below.

The electronic device 1 will be described herein below with particular reference to the FIGS. 3 and 4.

Referring back to FIG. 1, the system 100 further comprises a gymnastic machine 2 usable by the user for training.

To the purposes the present invention, by gymnastic machine is meant any machine usable by a user to perform a physical activity such as, for example, a treadmill (treadmill or tapis roulant), an exercise bike (cyclette) with an inclined seat, a traditional exercise bike, a muscle building equipment, and so on. The example of a gymnastic machine illustrated in FIG. 1 is a treadmill.

Figure 2:
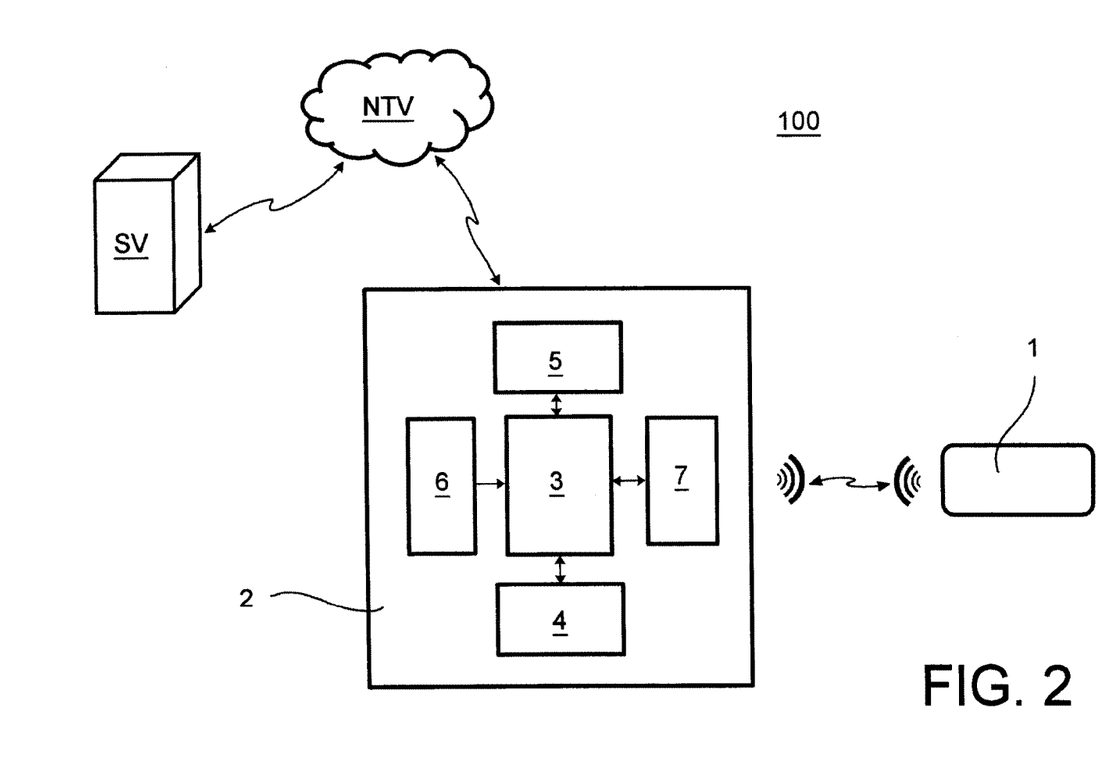
FIG. 2 schematically illustrates by a block diagram the system for controlling the training of FIG. 2.

With particular reference to FIG. 2, the gymnastic machine 2 comprises a main control unit 3, for example, a microcontroller or a microprocessor. Furthermore, the gymnastic machine 2 comprises a memory unit 4 operatively connected to the main control unit 3.

The main control unit 3 is configured to load and run one or more program codes (applications), stored in the memory unit 4, for controlling the gymnastic machine 2 before and/or during and/or after the training by the user. The memory unit 4 is configured to store, besides the above-mentioned program codes, the data processed by the main control unit 3 while running a program code.

Figure 1:
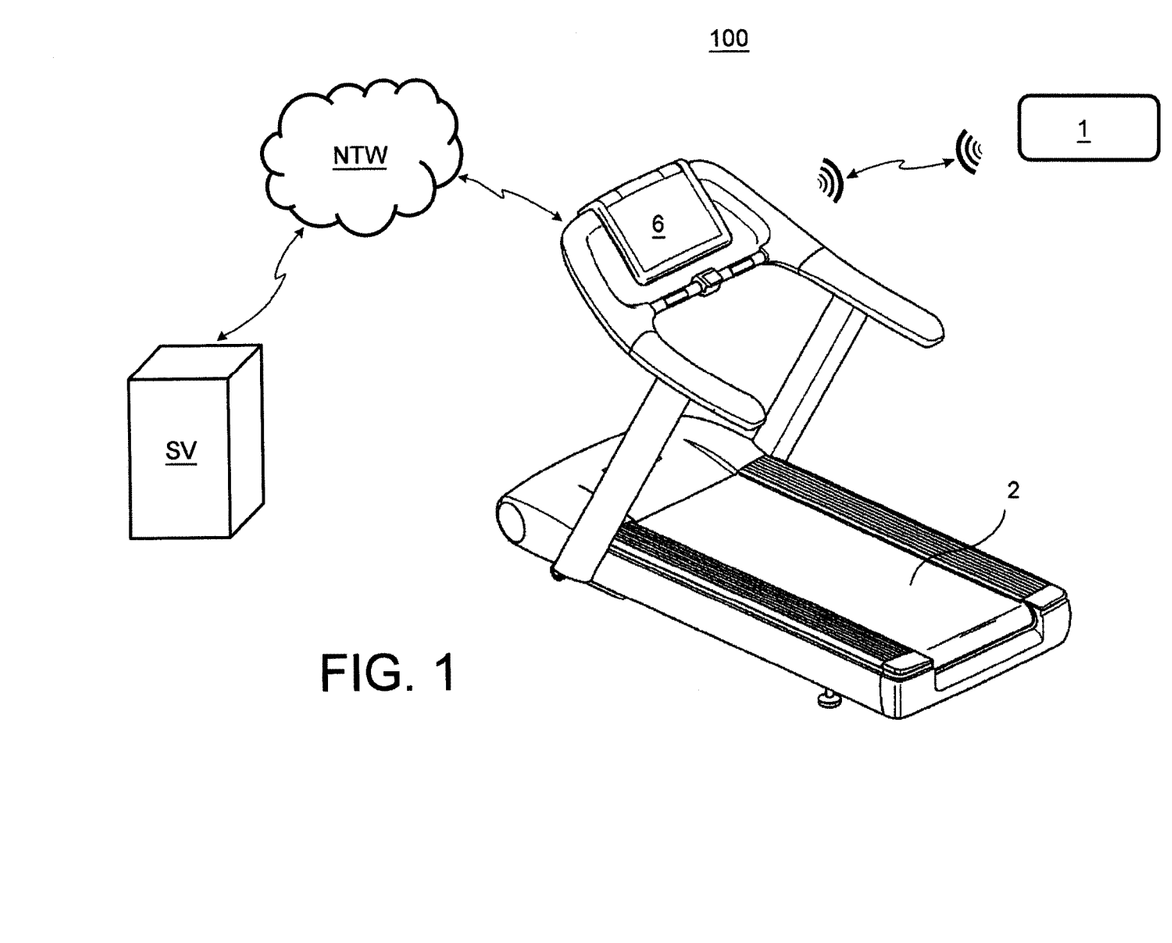
FIG. 1 schematically illustrates a system for controlling the training of a user on a gymnastic machine, according to an embodiment of the invention.

In accordance with the embodiment of FIG. 1, the gymnastic machine 2 further comprises a first data communication module 5, for example, a modem, operatively connected to the main control unit 3. Such data communication module 5 is configured to allow the main control unit 3 to be operatively connected, in a wireless or wired mode, to a data communication network NTW (shown schematically in FIG. 1), for example, the Internet network.

To this aim, as shown both in FIG. 1 and in FIG. 2, the system 100 further comprises a remote computer SV, for example, a server, which is also operatively connected, in a wireless or wired mode, to the data communication network NTW.

Therefore, the main control unit 3 of the gymnastic machine 2 is operatively connected to the remote computer SV.

In more detail, the main control unit 3 of the gymnastic machine 2 is configured to receive from the remote computer SV configuration parameters of the gymnastic machine 2 for carrying out a determined training by the authenticated user on the gymnastic machine 2.

With reference to the authentication of the user on the gymnastic machine 2, it is pointed out that, in an embodiment, the user can authenticate him/herself by interacting directly with the gymnastic machine 2.

In accordance with another embodiment, the user can authenticate him/herself by interacting with the gymnastic machine 2 through the electronic device 1 wearable by the user or, in accordance with another embodiment, by any other portable electronic device with which the user is provided, for example, a smartphone or a tablet.

It is pointed out that, in accordance with any of the embodiments hereto described, the main control unit 3 of the gymnastic machine 2, besides sending the user authentication data to the remote computer SV, and receiving from the remote computer SV the configuration parameters of the gymnastic machine for performing the determined training, is further configured to provide to the remote computer SV the user training data, during and/or after performing such training on the gymnastic machine 2.

In accordance with another embodiment, to be considered as an alternative or in combination with the one described above, the main control unit 3 of the gymnastic machine 2 is also further configured to provide the above-mentioned user training data, during and/or after performing such training on the gymnastic machine 2 to the electronic device 1 wearable by the user, as it will be described in detail herein below.

Referring back to the gymnastic machine 2 of the embodiment of FIGS. 1 and 2, it further comprises a control panel 6 operatively associated to the main control unit 3. Such control panel 6 is preferably provided with a displaying screen and with a respective control module (not shown in the Figures), for example, a keyboard arranged at the displaying screen or a virtual keyboard integrated in the displaying screen, in the case where the latter is of the touchscreen technology.

In the example of FIGS. 1 and 2, which is of the touchscreen technology, the control module of the control panel 6 coincides with the displaying screen (FIG. 1).

As already stated above, the user can authenticate him/herself before performing a training on the gymnastic machine 2, by interacting directly with the gymnastic machine 2. In the case of the embodiment of FIGS. 1 and 2, the user can interact with the gymnastic machine 2 through the control panel 6.

In a further embodiment (not shown in the Figures), the gymnastic machine 2 is without any control panels. In such a case, as it will be described herein below, the authentication of the user may occur through the electronic device 1 wearable by the user.

Referring back generally to the embodiment of FIG. 2, by virtue of the above-mentioned one or more program codes loadable in the memory unit 4 and runnable by the main control unit 3 of the gymnastic machine 2, the main control unit 3 of the gymnastic machine 2 is configured to receive from the electronic device 1, via a wireless-type data communication channel, an input command provided by the user to the electronic device 1. The definition of input command and examples of such input command will be provided herein below in the detailed description of the electronic device 1 wearable by the user.

Such wireless-type data communication channel is, for example, a Bluetooth technology data connection or a Wi-Fi technology data connection.

To this aim, the gymnastic machine 2 further comprises a second data communication module 7 operatively connected to the main control unit 3 of the gymnastic machine 2. The second data communication module 7 may be for example, of the type suitable to allow the creation of a Bluetooth technology data connection or of the type suitable to allow a Wi-Fi technology data connection, or both (Bluetooth and Wi-Fi).

In accordance with an embodiment, the main control unit 3 of the gymnastic machine 2 is further configured to form the wireless-type data communication channel with the electronic device 1 wearable by the user.

In more detail, it is pointed out that, in accordance with an embodiment, the main control unit 3 is advantageously configured to automatically detect the presence of the electronic device 1 wearable by the user to form the wireless-type data communication channel with the electronic device 1.

By automatically detect is meant, in the case of a Bluetooth technology data connection, that the gymnastic machine 2, since it has already created a Bluetooth technology data communication channel, is configured to detect the presence of the electronic device 1 worn by the user and to connect thereto through the existing Bluetooth technology data connection, or, in the case of a Wi-Fi technology connection, it is meant that the gymnastic machine 2, being already connected to a Wi-Fi technology data communication network, is configured to detect the electronic device 1 worn by the user and to connect thereto through the data connection to the Wi-Fi technology data communication network.

It shall be noticed that the automatic detection mode may be advantageously used, for example, in the case where the gymnastic machine 2 is without any control panel. However, such mode could by advantageously used also in the case where the gymnastic machine 2 is anyhow provided with a control panel 6.

In accordance with another embodiment, the main control unit 3 is advantageously configured to receive a tactile command from the user, for example, through the control panel 6, to form the wireless-type data communication channel with the electronic device 1 of the user. This detection mode can be used in the case where the gymnastic machine 2 is provided with a control panel 6.

In accordance with a further embodiment, the gymnastic machine 2 comprises an identification code (not illustrated in the Figures) detectable by the electronic device 1 of the user to form the wireless-type data communication channel with the electronic device 1 of the user.

The identification code may be any identification element of the gymnastic machine, such as a bar code (mono-dimensional or bi-dimensional, the latter being known as a QR code), a numeric code, an image, a graphic symbol, and so on. Such identification code may be applied on the gymnastic machine 2, for example, an adhesive applied on a structural element (a handle, stud, and so on) of the gymnastic machine, or, where present, displayed on the displaying screen (control panel 6).

Figure 3:
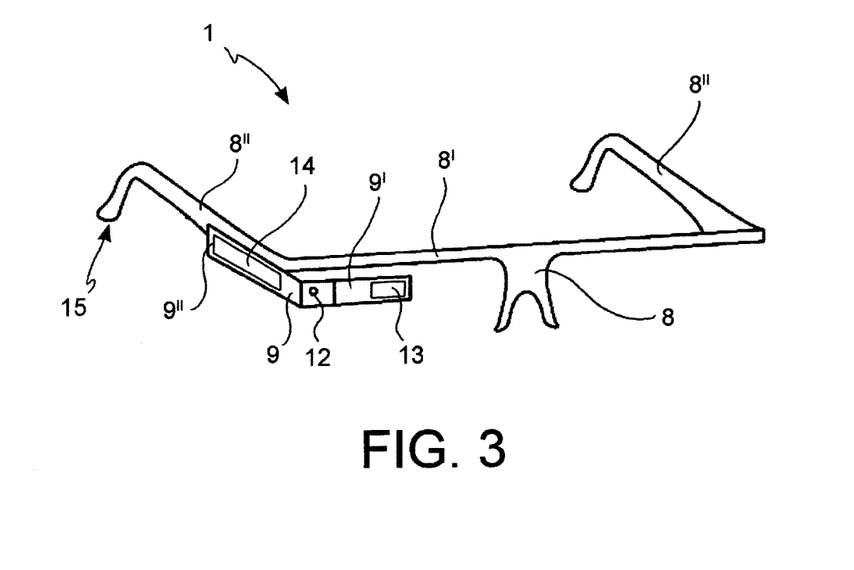
FIG. 3 illustrates an electronic device of the user usable in the system of FIG. 1, according to an embodiment of the invention.
Figure 4:
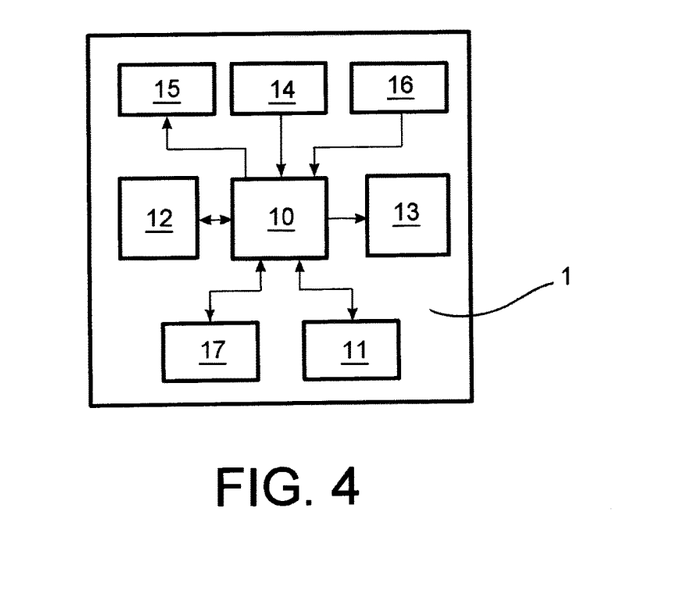
FIG. 4 schematically illustrates by a block diagram the electronic device of FIG. 3.

With particular reference to the FIGS. 3 and 4, the electronic device 1 wearable by the user, while performing the training, is now described.

With reference to FIG. 3, the electronic device 1 of the user comprises a support frame 8 that can be associated to the user's head (not shown in the Figures).

The support frame 8 advantageously comprises a central part 8' suitable to contact a portion of the user's face. Furthermore, the support frame 8 comprises a pair of side parts 8" suitable to contact respective side portions of the user's head in the proximity of the ears.

In more detail, each side part 8" has a first proximal end operatively connected to an end of the central part 8' of the support frame 8 and a second distal end, opposite the first proximal end, suitable to contact a respective side portion of the user's head at an ear.

In other terms, in the embodiment of FIG. 3, the support frame 8 has preferably a configuration completely similar to the frame of a pair of glasses.

In the example of FIG. 3, the support frame 8 is without lenses. However, in accordance with a further embodiment, the support frame 8 could be provided with lenses of a transparent material (for example, plastic, glass and so on).

Furthermore, in accordance with other embodiments, such support frame could have any other configuration such as to have, when the frame is associated to a person's head, at least one portion (central part) arranged at at least one eye of the person and at least one further portion (side part(s)) arranged at at least one ear of the person.

Referring back to the FIGS. 3 and 4, the electronic device 1 of the user further comprises a housing 9 suitable to house the electronic circuitry of the electronic device 1.

Such housing 9 is operatively connected to the support frame 8 preferably at the proximal end of a side part 8" of the support frame 8.

In more detail, such housing 9 is preferably L-shaped, and it extends, starting from such first proximal end, by a first portion 9' along the longitudinal development direction of the central part 8' of the support frame 8. Furthermore, such housing 9 extends, starting from such first proximal end, by a second portion 9" along the longitudinal development direction of the side part 8" of the support frame 8.

From a circuital point of view (FIG. 4), the electronic device 1 comprises a control module 10, for example, a microprocessor or a microcontroller, and a respective memory module 11, operatively connected to the control module 10.

The control module 10 is configured to load and run one or more program codes (applications), stored in the memory module 11, to manage the operation of the electronic device 1 and, as it will be described herein below, the control of the gymnastic machine 2 before and/or during and/or after the training by the user. The memory module 11 is configured to store, besides the above-mentioned program codes, the data processed by the control module 10 while running a program code. The control module 10 and the memory module 11 are not illustrated in FIG. 3.

The electronic device 1 further comprises a camera module 12, for example, a video camera, operatively connected to the control module 10. Such camera module 12, as shown schematically in FIG. 3, is preferably arranged on the central part 8' of the support frame 8. In more detail, the camera module 12 is arranged within the first portion 9' of the housing 9 of the support frame 8.

Furthermore, the electronic device 1 comprises an output module 13, 15 operatively connected to the control module 10 configured to allow the electronic device 1 interacting with the user. In fact, by output module is meant any electronic module configured to allow to the electronic device 1 providing information to the user.

In accordance with an embodiment, the output module comprises a displaying module 13.

The displaying module 13 is preferably arranged on the central part 8' of the support frame 8. In more detail, the displaying module 13 is arranged in the first portion 9' of the housing 9 of the electronic device 1. Furthermore, the displaying module 13 is advantageously arranged so as to be usable by an eye of the user, when the electronic device 1 is worn by the user.

In accordance with another embodiment, alternatively or in combination with the one described above, the output module 13, 15 further comprises a loudspeaker module 15, for example, a speaker.

The loudspeaker module 15 is suitable to provide the user with voice messages on the instruction of the control module 10. As it will be described herein below, the control module 10 is configured to generate said voice messages also based on instructions received from the gymnastic machine 2.

In accordance with an embodiment, the loudspeaker module 15 is advantageously arranged on one of the side parts 8" of the support frame 8 so that said loudspeaker module 15 is audible by an ear of the user.

For example, the loudspeaker module 15 may be arranged on the distal end of the side part 8" on which the second portion 9" of the housing 9 of the electronic device 1 (FIG. 3) is arranged.

According to other embodiments, not illustrated, the loudspeaker module 15 may be arranged on the side part 8" of the support frame 8 opposite the side part 8" on which the second portion 9" of the housing 9 is arranged, or it may be replicated also on such side part 8" of the support frame 8.

In accordance with another embodiment (also not shown in the Figures) the loudspeaker module 15 comprises at least one earpiece insertable into the user's ear and operatively connected (in a wired or wireless mode) to the electronic device 1 of the user.

Referring back generally to the electronic device 1, it further comprises an input module 14, 16 operatively connected to the control module 10 configured to allow the user interacting with the electronic device 1. In fact, by input module is meant an electronic module configured to allow the user providing input commands to the electronic device 1.

In an embodiment, the input module 14, 16 advantageously comprises a control touchpad 14 operatively connected to the control module 10.

The control touchpad 14 is configured to receive from the user input commands given with the fingers, for example, an instantaneous touch, double touch, scrolling (for example, with respect to the longitudinal development direction of the panel, top-down or vice versa, from the right side to the left side, or vice versa), and so on. The control module 10, through the program codes it can run, is also configured to convert such input commands into operative commands for the operation thereof and/or for the control and operation or the configuration of the gymnastic machine 2, as it will be described herein below.

In accordance with an embodiment, the control touchpad 14 is arranged on one of the side parts 8" of the support frame 8. This advantageously allows the user being able to provide to the electronic device 1 the above-mentioned input commands without partially or fully hiding the view of the user when the electronic device 1 is worn.

As shown in the example of FIG. 3, the control touchpad 14 is arranged in the second portion 9" of the housing 9.

In accordance with other embodiments, not shown in the Figures, the control touchpad 14 could by arranged in other parts of the support frame 8.

In accordance with a further embodiment, alternatively or in combination with those described above relative to the control touchpad 14, the input module 14, 16 further comprises a microphone 16.

Such microphone 16 is preferably arranged in the central part 8' of the support frame 8 so as to be able to detect the user's voice. In more detail, the microphone 16 (not shown in FIG. 3) is integrated in the first portion 9' of the housing 9 of the electronic device 1.

In accordance with other embodiments (not shown in the Figures), the microphone 16 may be integrated in other parts of the housing 9 of the electronic device 1, in other parts of the support frame 8 or in the earpiece (where present) used by the user to hear the voice messages generated by the electronic device 1.

In accordance with an embodiment, the electronic device 1 further comprises a further data communication module 17 operatively connected to the control module 10. The further data communication module 7 may be, for example, of the type suitable to allow the creation of a Bluetooth technology data connection or of the type suitable to allow a Wi-Fi technology data connection or both (Bluetooth and Wi-Fi).

In accordance with a further embodiment, the electronic device 1 further comprises at least one sensor (not shown in the Figures) configured to detect at least one physical parameter of the user during the training. Such at least one sensor is operatively connected to the control module 10 of the electronic device 1 of the user.

By a "physical parameter" of the user during the training is meant both a parameter representative of the physical movement of the user detectable during the training such as, for example, the frequency of the step, the oscillation of the head during the run or walk (in the case where the gymnastic machine 2 is a treadmill), and so on, and a parameter representative of the physical status of the user during the training, for example, the heart rate, the breathing frequency, the body temperature, and so on.

In accordance with an embodiment, said at least one sensor comprises at least one accelerometer, configured to detect particularly, among the physical parameters of the user during the training, the parameters representative of the user movement during the training. Such at least one accelerometer is preferably integrated in the housing 9 or the support frame 8 of the electronic device 1.

In accordance with a further embodiment, alternatively to the previous one, said at least one sensor may comprise, to the purposes detect particularly, among the user physical parameters during the training, those parameters representative of the physical status of the user during the training, at least one detection sensor of the heart rate.

Such at least one detection sensor of the heart rate is preferably integrated in the electronic device 1 at portions thereof brought to direct contact with the user.

For example, in the case of the Figures, in which the electronic device 1 comprises the support frame 8 in the shape of an eyeglass frame, the at least one detection sensor of the heart rate is preferably integrated in the central part 8' at the portion thereof intended to contact the nose or in the distal end of one or both side parts 8" at the portion thereof intended to contact the side part of the face, in the proximity of the ears, or within an earpiece in the case where the loudspeaker module 15 comprises at least one earpiece insertable in the user's ear, operatively connected (in a wired or wireless mode) to the electronic device 1 of the user.

In accordance with another embodiment, in combination or alternatively to those described above, the electronic device 1 further comprises at least one further sensor, operatively connected to the control module 10 of the electronic device 1 of the user. Such at least one further sensor may be, for example, a temperature sensor.

In accordance with another embodiment, the electronic device 1 of the user may comprise said at least one sensor, for example, an accelerometer, said at least one further sensor, for example, a detection sensor of the heart rate, and still a further sensor, for example, a temperature sensor.

In other embodiments, the electronic device 1 of the user may comprise a plurality of sensors, comprising several combinations of the sensors, some examples of which were provided above, in addition to one or more detection sensors of other physical parameters of the user.

The management and use, by the control module 10 of the electronic device 1 and by the main control unit 3 of the gymnastic machine 2, of the physical parameter detectable by said at least one sensor will be described herein below.

Referring back generally to the electronic device 1 wearable by the user, referring also to the system 100 of FIGS. 1 and 2, it is stated again that the control module 10 is configured to load and run program codes (applications) for controlling the gymnastic machine 2 before and/or during and/or after training of the user.

In more detail, the electronic device 1 is advantageously configured to provide the main control unit 3 of the gymnastic machine 2, through the wireless-type data communication channel, with an input command provided by the user to the electronic device 1.

To the purposes of the present description, by "input commands" which can be received by the electronic device 1 are meant commands that a user may generally provide to the electronic device 1, through the input module 14, 16.

Particularly, in accordance with an embodiment, such input command may be a tactile command provided by the user through the control touchpad 14. Examples of tactile command have been indicated above.

In accordance with another embodiment, such input command may be a vocal command provided by the user through the microphone 16.

In accordance with another embodiment, such input command may be a gestural command optically detected by the electronic device 1, for example, through the camera module 12. Examples of gestural command may be the movement of a hand from the right side to the left side, the movement of a hand from the left side to the right side, the movement of a hand moving near to the electronic device, the movement of a hand moving away from the electronic device 1.

Referring back to the wireless-type data communication between the electronic device 1 wearable by the user and the main control unit 3 of the gymnastic machine 2, it is pointed out that the control module 10 of the electronic device 1 wearable by the user is configured to form a wireless-type data communication channel with other electronic devices, such as the main control unit 3 of the gymnastic machine 2.

As already stated above, the wireless-type communication channel may be, in accordance with different embodiments, in the Bluetooth technology or Wi-Fi technology.

Some modes for enabling the above-mentioned data communication channel between the gymnastic machine 2 and the electronic device 1 wearable by the user, in accordance with different embodiments, have already been described above.

In a previous embodiment, the gymnastic machine 2 is advantageously configured to automatically detect the presence of the electronic device 1.

In accordance with a second embodiment, the detection of the presence of the electronic device 1, by the gymnastic machine 2, occurs only after a tactile command given by the user through the control panel 6 of the gymnastic machine 2.

In accordance with a third embodiment, the electronic device 1 is configured to detect, through the camera module 12, an identification code of the gymnastic machine 2. Following the detection of the identification code of the gymnastic machine 2, the electronic device 1 is configured to form the wireless-type data communication channel based on the above-mentioned identification code.

Examples of identification codes with which the gymnastic machine 2 may be provided, detectable by the camera module 12 of the electronic device 1, have been already indicated above.

In accordance with a further embodiment, it is pointed out that the electronic device 1 wearable by the user is configured to provide the main control unit 3 of the gymnastic machine 2, through the wireless-type data communication channel, with an authentication request command (LOGIN) on the gymnastic machine 2.

Examples of authentication request commands may be a vocal command (LOGIN) provided by the user at the microphone 16, or a tactile command provided by the user through the control touchpad 14 (for example, sliding a finger on the control touchpad 14).

On the other hand, as regards to the gymnastic machine 2, it is pointed out that the main control unit 3 is advantageously configured to generate, starting from said input command, an operative command to be provided to the gymnastic machine 2.

To the purposes of the present description, by "operative command to be provided to the gymnastic machine" is meant a command regarding the configuration and/or the operation of the gymnastic machine 2 before and/or during the training.

An operative command is as a function of the kind of gymnastic machine 2.

In the case where the gymnastic machine 2 is a treadmill, examples of an operative command to be provided to the gymnastic machine 2 are the operative start command (START), the operative stop command (STOP), the operative increasing speed command (INCREASING SPEED), the operative decreasing speed command (DECREASING SPEED), the operative increasing incline command (INCREASING INCLINE), the operative decreasing incline command (DECREASING INCLINE), and so on.

In the case where the gymnastic machine 2 is an exercise bike, examples of operative commands to be provided to the gymnastic machine 2 are the operative increasing resistance command (INCREASING RESISTANCE), the decreasing resistance command (DECREASING RESISTANCE), and so on.

In the case where the gymnastic machine is a muscle building equipment, in which it is possible to automatically change the weight (e.g., gravitational), examples of operative commands to be provided to the gymnastic machine 2 are the operative increasing weight command (INCREASING WEIGHT), the operative decreasing weight command (DECREASING WEIGHT), and so on.

In accordance with an embodiment, in the case where the input command provided by the user to the electronic device 1 is a vocal command, the main control unit 3 of the gymnastic machine 2 is configured to interpret such vocal command, to the purpose of generating, starting from said input command, an operative command to be provided to the gymnastic machine 2, by using a dedicated speech recognition program code stored in the memory unit 4 of the gymnastic machine 2.

In accordance with another embodiment, alternative to the previous one, in the case where the input command provided by the user to the electronic device 1 is a vocal command, the main control unit 3 of the gymnastic machine 2 is configured to interpret such vocal command, to the purpose of generating, starting from said input command, an operative command to be provided to the gymnastic machine 2, by using a dedicated WEB service usable on-line, for example, through the Internet network. In other terms, in order to interpret the vocal command, the main control unit 3 of the gymnastic machine 2 is configured to require a connection to the data communication network NTW (Internet) and to be able to use the above-mentioned WEB service for interpreting vocal commands.

By comparing the two alternative embodiments just described, it is apparent that the embodiment using a dedicated speech recognition program code stored in the memory unit 4 of the gymnastic machine 2 advantageously allows using the gymnastic machine 2 through the electronic device 1 also in the case where the gymnastic machine 2 is not connected to the data communication network NTW or the data connection to such data communication network NTW is out of order or temporarily unavailable.

In accordance with other embodiments, in the case where the input command provided by the user to the electronic device 1 is a tactile command or a gestural command, the main control unit 3 of the gymnastic machine 2 is configured to generate the operative command to be provided to the gymnastic machine 2, based on the input command provided by the user to the electronic device 1, using dedicated program codes for recognizing tactile commands inserted via the touchpad or using dedicated program codes for recognizing gestural commands, both storable in the memory unit 4 of the gymnastic machine 2.

In accordance with another embodiment, such dedicated program codes for recognizing tactile commands inserted via the touchpad or said dedicated program codes for recognizing gestural commands are usable on-line, for example, through the connection to the Internet network.

Referring back generally to the embodiment of FIGS. 1 and 2, the main control unit 3 is configured to control the gymnastic machine 2 based on said operative command.

Furthermore, based on what has been already stated above, the main control unit 3 of the gymnastic machine 2 is also configured to authenticate the user on the gymnastic machine 2 based on the authentication request command (LOGIN) provided by the user, through the electronic device 1 wearable by the user.

In accordance with a further embodiment, the main control unit 3 of the gymnastic machine 2 is further configured to provide to the electronic device 1 of the user, through the wireless-type data communication channel, data representative of the training being performed by the user on the gymnastic machine 2.

The data representative of the training being performed by the user on the gymnastic machine 2 is as a function of the kind of gymnastic machine 2.

In the case where the gymnastic machine is a treadmill and the training consists in a run/walk thereon, such data will be, for example, run or walk speed, stride and/or width and/or frequency of the step of a run or walk, the distance covered, the distance to be covered, training time, indication of the correctness or not of the posture during the run or walk, motivational messages on the quality of the exercise being carried out, and so on.

In the case where the gymnastic machine is an exercise bike, such data will be, for example, pedal speed, pedal frequency, the distance covered, the distance to be covered, training time, resistance, indication of the correctness or not of the posture, motivational messages on the quality of the exercise being carried out, and so on.

In the case where the gymnastic machine is a muscle building equipment, such data will be, for example, the weight, the number of repetitions performed, the number of repetitions to be performed, the indication of the correctness or not of the posture while performing the exercise, motivational messages on the quality of the exercise being carried out and so on.

In accordance with an embodiment of the gymnastic machine 2, to be considered in combination with any of those described above, the main control unit 3 is further configured to provide advantageously to the electronic device 1 of the user, through the wireless-type data communication channel, data representative of the changes of the training parameters of the user on the gymnastic machine.

Also the training parameters are as a function of the kind of gymnastic machine.

In the case where the gymnastic machine 2 is a treadmill, a training parameter to be changed may be, for example, the speed of the treadmill.

In the case where the gymnastic machine 2 is an exercise bike, a training parameter to be changed may be, for example, the resistance.

In the case where the gymnastic machine 2 is a muscle building equipment, a training parameter to be changed may be, for example, the weight to be loaded.

Referring back to the electronic device 1 of the user, the control module 10 of the electronic device 1 of the user is further configured to receive from the main control unit 3 of the gymnastic machine 2 the data representative of the training being performed by the user on the gymnastic machine, described and defined above.

Furthermore, the control module 10 of the electronic device 1 of the user is also configured to provide to the user the data representative of the training being performed by the user on the gymnastic machine 2.

Particularly, in accordance with an embodiment, the control module 10 of the electronic device 1 of the user is configured to display such data representative of the training being performed by the user on the gymnastic machine 2 on the output module 13, 15 of the electronic device 1 of the user, for example, on the displaying module 13.

In accordance with a further embodiment, alternatively or in combination with the one described above, the control module 10 of the electronic device 1 of the user is also configured to reproduce such data representative of the training being performed by the user on the gymnastic machine 2 through the output module 13, 15 of the electronic device 1 of the user, for example, through the loudspeaker module 15.

Both the embodiments described above allow advantageously the user to be able to know the data representative of the training in a very simple mode (video and/or audio). Particularly, the fact that such data may be displayed on the output module 13, 15 (for example, the displaying module 13) of the electronic device 1 of the user, arranged in the proximity of the user's eye (as indicated above) advantageously allows the user to be able to continue his/her training without changing the posture, e.g., avoiding to point his/her look downwardly to read a display with which the gymnastic machine 2 could be provided. Of course, the same advantage is achieved also by the embodiment in which such data is provided to the user through the output module 13, 15 of the electronic device 1, for example, in the case where the output module 13, 15 is a loudspeaker module 15.

Furthermore, in accordance with another embodiment, the control module 10 of the electronic device 1 of the user is configured to receive from the main control unit 3 of the gymnastic machine 2 the data representative of the changes of the training parameters of the user on the gymnastic machine 2, already described and defined above.

In such a case, the control module 10 of the electronic device 1 is configured to provide the user with the data representative of the changes of the training parameters of the user on the gymnastic machine 2.

This characteristic advantageously allows the user to be informed in time of the change of the training program, thus making the use of the gymnastic machine 2 safer and, at the same time, making the training method more efficient.

In accordance with an embodiment, the control module 10 of the electronic device 1 of the user is configured to display such data representative of the changes of the training parameters of the user on the gymnastic machine 2 on the output module 13, 15 (for example, the displaying module 13) of the electronic device 1 of the user.

In accordance with a further embodiment, alternatively or in combination with the one described above, the control module 10 of the electronic device 1 of the user is configured to reproduce such data representative of the changes of the training parameters of the user on the gymnastic machine 2 through the output module 13, 15 of the electronic device 1 of the user, in the case where such output module 13, 15 is the loudspeaker module 15.

Also both the embodiments described above allow advantageously the user to be able to know the data representative of the changes of the training parameters in a very simple manner (video and/or audio). Particularly, the fact that such data may be displayed on the output module 13, 15 (displaying module 13) of the electronic device 1 of the user, arranged in the proximity of the user's eye (as indicated above) advantageously allows the user to be able to continue the training without changing his/her posture, avoiding to point for example his/her look downwardly to read a display with which the gymnastic machine 2 could be provided. Of course, the same advantage is achieved also by the embodiment in which such data is provided to the user through the output module 13, 15 of the electronic device 1, also in the case where it is the loudspeaker module 15.

It is pointed out that such data may be generated by the main control unit 3 of the gymnastic machine 2 in the case where the user is performing a training that provides for carrying out a determined training program stored in the memory unit 4 of the gymnastic machine 2. For example, a training program on a treadmill may provide for that in a determined time moment, the incline or slope of the treadmill may be changed automatically. According to another example, a training program on an exercise bike may provide for that, in a determined time moment, the pedal ramp, i.e., the resistance, may be changed automatically.

Alternatively, such data could be generated by the main control unit 3 of the gymnastic machine 2 as a response to an input command provided by the user through the electronic device 1. Such input command could be a vocal command, a tactile command, or a gestural command, as defined above.

Referring back to the gymnastic machine 2, it is pointed out that the main control unit 3 of the gymnastic machine 2 is advantageously configured to send to the electronic device 1 wearable by the user, through the wireless-type data communication channel, configuration parameters of the electronic device 1 based on the kind of gymnastic machine 2, of the kind of the training by the user on such gymnastic machine 2 and of the kind of user.

Furthermore, the electronic device 1 of the user so configured is also changeable, by the user, by customizing settings, training programs, and so on.

Furthermore, the electronic device 1 of the user is advantageously configured to provide to the main control unit 3 of the gymnastic machine 2 the configuration parameters of the gymnastic machine 2 for carrying out a training by the user on such gymnastic machine 2. Such configuration parameters may be loaded by the user on the electronic device 1 of the user in another mode (for example, with a wired connection or another Bluetooth connection).

In accordance with a further embodiment, the electronic device 1 is configured to provide to the main control unit 3 of the gymnastic machine 2 at least one physical parameter of the user during the training (defined above) detected through said at least one sensor.

To this aim, the main control unit 3 of the gymnastic machine 2 is configured to receive from the electronic device 1, through the wireless-type data communication channel, said at least one physical parameter of the user.

In accordance with such embodiment, the main control unit 3 of the gymnastic machine 2 is configured to generate, based on said at least one physical parameter received, an operative command of the gymnastic machine 2, by running a dedicated program code with which it is provided.

Examples of operative command of the gymnastic machine 2 have been already defined above.

The main control unit 3 of the gymnastic machine 2 is advantageously configured to control the gymnastic machine 2 based on the generated operative command.

Examples of operative command of the gymnastic machine 2 have been already defined above.

By way of example, in the case where the physical parameter detected and sent to the gymnastic machine 2 is the heart rate, the main control unit 3 may advantageously control the gymnastic machine 2 as a function of the heart rate, for example, by decreasing the speed of a treadmill in the moment when the heart rate exceeds a baseline value that is safe for the user.

This allows advantageously being able to ensure a higher safety level of the training by the user, from a physical point of view.

In accordance with a further embodiment, to be considered in combination with the one just described, in the case where the input command received from the electronic device 1 (either it is a vocal command, a tactile command, or a gestural command) is the request of a physical parameter of the training of the user, the gymnastic machine 2 is configured to provide to the electronic device 1, through the wireless-type data communication channel, the required physical parameter, selected among those received by the electronic device 1.

The modes with which the control module 10 of the electronic device 1 provides such physical parameter to the user are completely similar to those described in accordance with the embodiments described above with reference to the use, by the user, through the electronic device 1, of the data representative of the training being performed by the user on the gymnastic machine 2 or the data representative of the changes of the training parameters of the user on the gymnastic machine 2.

In accordance with such embodiment, the main control unit 3 of the gymnastic machine 2 is configured to generate, based on said at least one physical parameter received, an operative command of the gymnastic machine 2.

In accordance with a further embodiment of the system 100, the control module 10 of the electronic device 1 wearable by the user is configured to store images representative of the visual perspective of the user while carrying out a training without the aid of a gymnastic machine 2 (training outdoor), for example, a run or walk or pedal outdoor. The images representative of the visual perspective of the user may be acquired through the camera module 12 with which the electronic device 1 is provided. Such images may be photographs or a movie.

In accordance with this embodiment, the system 100 further comprises a satellite receiving module (GPS) configured to acquire information representative of the path followed by the user while carrying out the training. Such information are for example, the position and movements of the user, the path length, the slope of the terrain, and so on.

In an embodiment, the satellite receiving module (GPS) is integrated in the electronic device 1 of the user.

In accordance with a further embodiment, alternative to the previous one, the satellite receiving module (GPS) may be integrated in any other portable electronic device with which the user may be provided during the training, for example, a smartphone (smartphone), a watch, a multimedia file reader (for example, MP3 files), a pedometer, and so on.

Referring back generally to the embodiment of the system 100 described, the main control unit 3 of the gymnastic machine 2 is configured to receive from the electronic device 1, through the wireless-type data communication channel, the images representative of the visual perspective of the user while carrying out a training.

Furthermore, the main control unit 3 of the gymnastic machine 2 is configured to receive from the satellite receiving module (GPS) information representative of the path followed by the user while carrying out the training.

In accordance with a previous embodiment, in the case where such satellite receiving module (GPS) is integrated in the electronic device 1 of the user, the main control unit 3 of the gymnastic machine 2 is configured to receive from the satellite receiving module (GPS) information representative of the path followed by the user while carrying out the training through the wireless-type data communication channel.

In accordance with a second embodiment, in the case where such satellite receiving module (GPS) is integrated in a further portable electronic device of the user, the main control unit 3 of the gymnastic machine 2 is configured to receive such information from a remote server, through the data communication network NTW, in which such information has been previously transferred from the further portable electronic device of the user.

Referring back generally to the embodiment of the system 100, the main control unit 3 of the gymnastic machine 2 is also configured to simulate on the gymnastic machine 2, based on the images representative of the visual perspective of the user and the received information representative of the path followed by the user while performing the training, which training is being performed by the user outdoor.

In more detail, to this aim, the main control unit 3 of the gymnastic machine 2 is also configured to:
  generate, based on the images representative of the visual perspective of the user and the received information representative of the path followed by the user while performing the training, operative commands of the gymnastic machine 2;
  control the gymnastic machine 2 based on the operative commands generated.

In addition, in accordance with an embodiment, the main control unit 3 of the gymnastic machine 2 may be optionally configured to provide to the electronic device 1, through the wireless-type data communication channel, the images representative of the training performed by the user outdoor.

In accordance with another embodiment, the main control unit 3 of the gymnastic machine 2 may be configured to provide the images representative of the training performed by the user outdoor through the displaying screen with which the control panel 6 of the gymnastic machine 2 is optionally provided.

In such a manner, the user will be able not only to simulate the training outdoor not only from the point of view of the physical strain, but also of the outdoor view.

Figure 5:
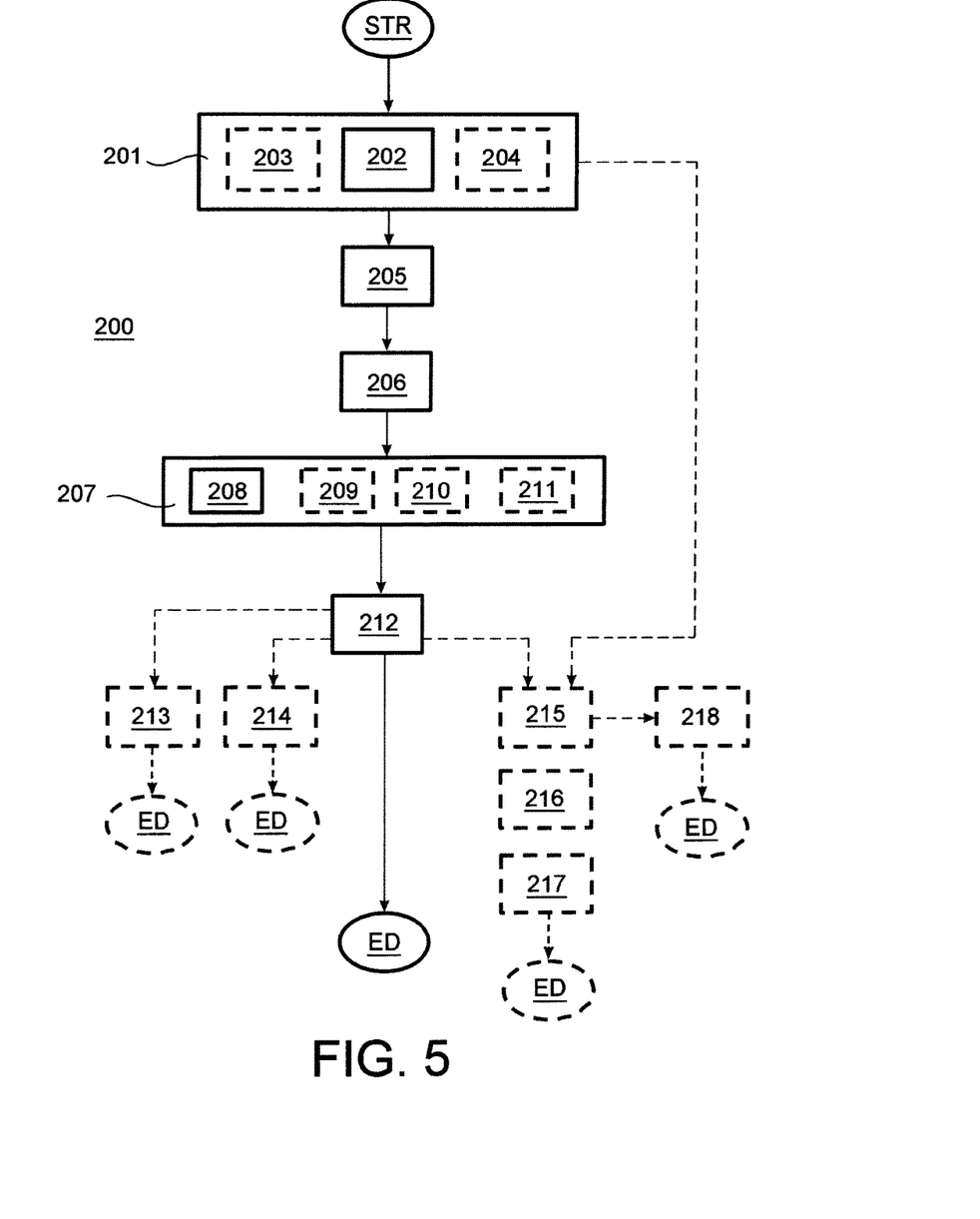
FIG. 5 schematically illustrates by a block diagram a method for controlling the training of the user on a gymnastic machine, according to an embodiment of the invention.

With reference again to the FIGS. 1-4 and also to FIG. 5, a method is now described for controlling a gymnastic machine 2 usable by a user for a training. Such method for controlling, herein below also simply method, is indicated in FIG. 5 with the numeral reference 200.

As stated several times above, the user is provided with an electronic device 1 wearable by the user, which is configured to receive commands by the user.

The method 200 comprises a symbolic step of starting STR.

The method 200 further comprises a step of forming 201, by the main control unit 3 of the gymnastic machine 2, a wireless-type data communication channel with said electronic device 1 wearable by the user.

In accordance with an embodiment, the step of forming 201 comprises a step of automatically detecting 202, by the main control unit 3 of the gymnastic machine 2, the presence of the electronic device 1 wearable by the user. The definition of automatically detecting has been already defined above.

In accordance with a further embodiment, alternative to the one indicated above, the step of forming 201 comprises a step of providing 203 to the main unit 3 of the gymnastic machine 2, by the user, a tactile command. Such tactile command may be provided by interacting, for example, with the control panel 6 with which the gymnastic machine 2 may be provided.

In accordance with a further embodiment, the step of forming 201 comprises a step of providing 204, by the gymnastic machine 2, an identification code of the gymnastic machine 2 optically detectable by the electronic device 1 wearable by the user, for example, through the camera module 12. Examples of identification codes have been indicated above.

In accordance with an embodiment (shown in the Figures), it is pointed out that the method 200 comprises, subsequently to the step of forming 201, a step of authenticating 205 the user on the gymnastic machine 2. Some authentication modes of the user on the gymnastic machine 2 have been described above.

However, it is pointed out that the step of authenticating 205 is optional. In accordance with other embodiments (not shown), the method 200 may be without such step of authenticating.

The method 200 further comprises a step of receiving 206, by the main control unit 3 of the gymnastic machine 2, from said electronic device 1 wearable by the user, through the wireless-type data communication channel, an input command provided by the user to the electronic device 1 wearable by the user.

To this aim, examples of input command, already defined and described above, may be: a vocal command, tactile command provided through the control touchpad 14 of the electronic device 1 wearable by the user, a gestural command optically detected by the electronic device 1 wearable by the user, through the camera module 12 with which the electronic device 1 is provided.

Furthermore, the method 200 further comprises the step of generating 207, by the main control unit 3 of the gymnastic machine 2, based on the received input command, an operative command of the gymnastic machine 2.

The definition of operative command and some possible examples have been provided above.

In accordance with an embodiment, in the case where the input command is a vocal command, the step of generating 207 comprises a step of interpreting 208, by the main control unit 3 of the gymnastic machine 2, the input vocal command received through a respective speech recognition program code stored in the memory unit 4 of the gymnastic machine 2.

In accordance with another embodiment, alternative to the previous embodiment, in the case where the input command is a vocal command, the step of generating 207 comprises a step of interpreting 209, by the main control unit 3 of the gymnastic machine 2, the input vocal command received by using a dedicated WEB service usable on-line, for example, through the Internet network.

In accordance with an embodiment, in the case where the input command is a tactile or a gestural command, the step of generating 207 comprises a step of interpreting 210, by the main control unit 3 of the gymnastic machine 2, the input tactile command received via a program code for recognizing tactile commands inserted through the touchpad, or the gestural command received via a program code dedicated for recognizing gestural commands, said program codes being stored in the memory unit 4 of the gymnastic machine 2.

In accordance with an embodiment, in the case where the input command is a tactile or a gestural command, the step of generating 207 comprises a step of interpreting 211, by the main control unit 3 of the gymnastic machine 2, the input tactile command received via a program code for recognizing tactile commands inserted through the touchpad, or the gestural command received via a program code dedicated for recognizing gestural commands, said program codes being usable on-line, for example, through the connection to the Internet network.

Subsequently, the method 200 further comprises a step of controlling 212, by the main control unit 3 of the gymnastic machine 2, the gymnastic machine based on the generated operative command.

Advantageously, in a further embodiment, the method 200 further comprises a step of providing 213 to the electronic device 1 wearable by the user, through the wireless-type data communication channel, by the main control unit 3 of the gymnastic machine 2, data representative of the training being performed by the user on the gymnastic machine. Examples of such data have been provided above.

Again, in another embodiment, alternatively (shown in FIG. 5) or in combination with the previous one, the method 200 further comprises a step of providing 214 to the electronic device 1 wearable by the user, through the wireless-type data communication channel, by the main control unit 3 of the gymnastic machine 2, data representative of the changes of the training parameters of the user on the gymnastic machine. Examples of the above-mentioned data have been indicated above.

In accordance with a further embodiment, in combination or alternatively (shown in FIG. 5) to the one described above, the method 200 further comprises a step of receiving 215 from the electronic device 1 wearable by the user, by the main control unit 3 of the gymnastic machine 2, through the wireless-type data communication channel, at least one physical parameter of the user detected by at least one sensor with which is provided the electronic device 1 of the user.

It shall be noticed that, in another embodiment (shown in the FIG. 5) the step of receiving 215 may occur just following the step of forming 201, by the main control unit 3 of the gymnastic machine 2, a wireless-type data communication channel, with the electronic device 1.

Subsequently, the method 200 comprises a step of generating 216, by the main control unit 3 of the gymnastic machine 2, based on said at least one physical parameter received, an operative command of the gymnastic machine 2, by running a dedicated program code with which the main control unit 3 of the gymnastic machine 2 is provided. Examples of operative command of the gymnastic machine 2 have been already defined above.

Next, the method 200 further comprises a step of controlling 217 the gymnastic machine 2, by the main control unit 3 of the gymnastic machine 2, based on the generated operative command.

In accordance with a further embodiment, in the case where the input command received from the electronic device 1 (whether it is a vocal command, a tactile command, or a gestural command) is the request of at least one physical parameter of the training of the user, the method 200 comprises a step of providing 218 to the electronic device 1, by the main control unit 3 of the gymnastic machine 2, through the wireless-type data communication channel, said at least one required physical parameter, selected among those received by the electronic device 1.

It shall be noticed that the modes with which the control module 10 of the electronic device 1 provides such at least one physical parameter of the user are completely similar to those described in accordance with the embodiments described above with reference to the use, by the user, through the electronic device 1, of the data representative of the training being performed by the user on the gymnastic machine 2 or the data representative of the changes of the training parameters of the user on the gymnastic machine 2.

In accordance with the embodiments described above, the method ends with a symbolic step of ending ED (FIG. 5).

Finally, it shall be noticed that a code or program product is loadable in a memory unit of a computer, for example, in the memory unit 4 of the gymnastic machine 2 (operatively connected to the main control unit 3 of the gymnastic machine 2), to carry out the steps of the method for controlling 200 according to the different embodiments described above.

With reference to the above-mentioned figures, an example of operation of the system 100 is now described, in the case where the electronic device 1 wearable by the user has a support frame 8 completely similar to an eyeglass frame.

The user wears the electronic device 1.

Subsequently, the user, by moving the electronic device 1 near to the gymnastic machine 2 (for example, a treadmill), automatically creates the wireless-type data communication channel (for example, Bluetooth) between the electronic device 1 and the gymnastic machine 2.

Next, the user optionally carries out the authentication on the gymnastic machine 2 (optional selection) and configures the gymnastic machine 2 with a determined program training (for example, a run) customized to him/her.

Subsequently, the user, through the electronic device 1 worn, provides a voice-type input command to start the training.

The gymnastic machine 2, once it has received and interpreted the input command, by a dedicated program code stored in the memory unit 4 of the gymnastic machine 2 or usable through the connection, via the Internet network, to a dedicated WEB service, generates an operative command that actuates the treadmill for a training.

During the run, the user displays on the output module 13, 15 (displaying module 13) of the electronic device 1 the data representative of the training being carried out on the gymnastic machine 2 (for example, speed, the distance covered, running time, and so on).

During the run, the gymnastic machine 2, through the output module 13, 15 (loudspeaker module 15) with which the electronic device 1 worn by the user is provided, sends to the user incentivizing and motivational messages relating to the proper body posture while running.

When the user decides to increase the running speed, the user provides an input command to the electronic device 1, through the input module 14, 16, for example, by touching the control touchpad 14, of the electronic device 1 to require the speed increase.

The gymnastic machine 2, once it has received said input command, generates the corresponding operative command of the gymnastic machine 2 and actuates the gymnastic machine 2 so as to increase the treadmill rotational speed. Simultaneously, the gymnastic machine 2 sends to the electronic device 1 a datum representative of the speed change. The electronic device 1 emits a vocal message, through the output module 13, 15 (loudspeaker module 15), in which it indicates the speed change to the user.

At the end of the training, the user sends a voice-type input command to end the training.

The gymnastic machine 2 receives and interprets the vocal command, by a dedicated program code stored in the memory unit 4 of the gymnastic machine 2 or usable through the connection, via the Internet network, to a dedicated WEB service, generates the corresponding operative command and stops the rotation of the treadmill.

The user leaves the gymnastic machine 2 and removes the electronic device 1 which he/she was wearing.

As it can be noticed, the object of the invention is fully achieved.

In fact, the gymnastic machine, the system and the method for controlling a user training described have a number of advantages, all of which are aimed to simplify the control of the user training on the gymnastic machine.

First of all, the possibility to send commands to the gymnastic machine by interacting directly with the electronic device worn, through the voice or a simple touch, allows the user controlling the gymnastic machine in a simple, intuitive, and direct manner, avoiding having to interact with a control panel of the gymnastic machine.

Furthermore, the fact of limit the use of the hands to interact to the maximum extent with the electronic device worn allows the user maintaining a proper and safe position at best while performing the training.

Again, the fact that the commands may be given by one's voice makes the control mode very simple and suitable also to user with a lesser familiarity with a more advanced technology.

In addition, the fact that a feedback relative to the data representative of the training or the changes of the training parameters is usable directly through the electronic device, also in the presence of a gymnastic machine without a display, allows a user, also skilled, to know in real time how the training is progressing, the possible posture changes that optionally have to be adopted (where necessary), and so on, without having to wait, in some cases, for the completion of the training.

Next, the fact that the enabling of the wireless-type data communication channel and the successive authentication of the user may be carried out with the modes described above makes the proposed technical solution very simple and intuitive.

Furthermore, the fact that a feedback on the physical parameters of the user while performing the training is usable directly through the electronic device, both on the initiative of the gymnastic machine 2 and on a request by the user through the electronic device 1, allows a user, also skilled, to know and control in real time both the body movement and the physical status (hence, the health conditions) while performing the training, avoiding undue stresses and preserving his/her own health.

To the embodiments of the gymnastic machine, the system, the method, and the program product for the control of the training of the user on the gymnastic machine, described above, those skilled in the art, in order to meet contingent needs, will be able to make modifications, adaptations, and replacements of elements with functionally equivalent other ones, without departing from the scope of the following claims. Each of the characteristics described as belonging to possible embodiment may be carried out independently from the other embodiments described.

The invention claimed is:

1. Gymnastic machine usable by a user for a training, said user being provided with an electronic device wearable by the user, which is configured to receive commands by the user, said gymnastic machine comprising a main control unit configured to:
    form a wireless-type data communication channel with said electronic device;
    receive from said electronic device, through the wireless-type data communication channel, an input command provided by the user to the electronic device, wherein said input command of the gymnastic machine received by the control unit of the gymnastic machine comprises at least one of a vocal command, a tactile command on the electronic device, or a gestural command optically detected by the electronic device;
    generate, based on the received input command, an operative command of the gymnastic machine;
    control the gymnastic machine based on said generated operative command,
    wherein, in the case that the input command provided by the user to the electronic device is a vocal command, the main control unit of the gymnastic machine is configured to interpret such vocal command, to the purpose of generating, starting from said input command, an operative command to be provided to the gymnastic machine, by using a dedicated speech recognition program code stored in a memory unit of the gymnastic machine.

2. Gymnastic machine according to claim 1, wherein the main control unit is configured to automatically detect the presence of the electronic device of the user to form the wireless-type data configuration channel with the electronic device of the user.

3. Gymnastic machine according to claim 1, wherein the main control unit is configured to receive a tactile command from the user to form the wireless-type data configuration channel with the electronic device of the user.

4. Gymnastic machine according to claim 1, comprising an identification code optically detectable by the electronic device of the user to form the wireless-type data communication channel with the electronic device of the user.

5. Gymnastic machine according to claim 1, wherein the main control unit is further configured to provide the electronic device of the user, through the wireless-type data communication channel, with data representative of the training being performed by the user on the gymnastic machine.

6. Gymnastic machine according to claim 1, wherein the main control unit is further configured to provide the electronic device of the user, through the wireless-type data communication channel, with data representative of the changes of the training parameters of the user on the gymnastic machine.

7. Gymnastic machine according to claim 1, wherein the main control unit is configured to receive from the electronic device of the user, through the wireless-type data communication channel, at least one physical parameter of the user detectable by at least one sensor with which the electronic device of the user is provided.

8. Gymnastic machine according to claim 7, wherein the main control unit of the gymnastic machine is configured to generate, based on said at least one physical parameter received, an operative command of the gymnastic machine.

9. Gymnastic machine according to claim 8, wherein the main control unit of the gymnastic machine is configured to control the gymnastic machine based on the generated operative command.

10. Gymnastic machine according to claim 1 wherein, in the case that the input command provided by the user to the electronic device is a tactile command or a gestural command, the main control unit of the gymnastic machine is configured to generate the operative command to be provided to the gymnastic machine, based on the input command provided by the user to the electronic device, by using dedicated program codes for recognizing tactile commands inserted via the touchpad, or by using dedicated program codes for recognizing gestural commands, both storable in a memory unit of the gymnastic machine.

11. System for controlling the training of a user, comprising:
an electronic device wearable by a user; and
a gymnastic machine usable by a user for a training, said user being provided with the electronic device wearable by the user, which is configured to receive commands by the user, said gymnastic machine comprising a main control unit configured to:
form a wireless-type data communication channel with said electronic device;
receive from said electronic device, through the wireless-type data communication channel, an input command provided by the user to the electronic device, wherein said input command of the gymnastic machine received by the control unit of the gymnastic machine comprises at least one of a vocal command, a tactile command on the electronic device, or a gestural command optically detected by the electronic device;
generate, based on the received input command, an operative command of the gymnastic machine;
control the gymnastic machine based on said generated operative command,
wherein, in the case that the input command provided by the user to the electronic device is a vocal command, the main control unit of the gymnastic machine is configured to interpret such vocal command, to the purpose of generating, starting from said input command, an operative command to be provided to the gymnastic machine, by using a dedicated speech recognition program code stored in a memory unit of the gymnastic machine.

12. Method for controlling a gymnastic machine usable by a user for the training, said user being provided with an electronic device wearable by the user, which is configured to receive commands by the user, said method comprising steps of:
forming, by the main control unit of the gymnastic machine, a wireless-type data communication channel with said electronic device wearable by the user;
receiving, by the main control unit of the gymnastic machine, through the wireless-type data communication channel, from said electronic device wearable by the user, an input command provided by the user to the electronic device wearable by the user, wherein said input command provided by the electronic device of the user wearable by the user comprises at least one of a vocal command, a tactile command on the electronic device wearable by the user, or a gestural command optically detected by the electronic device wearable by the user;
generating, by the main control unit of the gymnastic machine, based on the received input command, an operative command of the gymnastic machine;
controlling, by the main control unit of the gymnastic machine, the gymnastic machine based on the generated operative command, wherein, in the case that the input command is a vocal command, the step of generating comprises a step of interpreting, by the main control unit of the gymnastic machine, the input vocal command received via a respective speech recognition program code stored in the memory unit of the gymnastic machine.

13. Method according to claim 12, wherein the step of forming comprises a step of automatically detecting, by the main control unit of the gymnastic machine, the presence of the electronic device wearable by the user.

14. Method according to claim 12, wherein the step of forming comprises a step of providing the main control unit of the gymnastic machine, by the user, with a tactile command.

15. Method according to claim 12, wherein the step of forming comprises a step of providing, by the gymnastic machine, an identification code of the gymnastic machine optically detectable by the electronic device wearable by the user.

16. Method according to claim 12, further comprising a step of providing the electronic device wearable by the user, through the wireless-type data communication channel, by the main control unit of the gymnastic machine, with data representative of the training being performed by the user on the gymnastic machine.

17. Method according to claim 12, further comprising a step of receiving from the electronic device wearable by the user, by the main control unit of the gymnastic machine, through the wireless-type data communication channel, at least one physical parameter of the user detected by at least one sensor with which the electronic device of the user is provided.

18. Method according to claim 17, further comprising the step of:
generating, by the main control unit of the gymnastic machine, based on said at least one received physical parameter, an operative command of the gymnastic machine, running a dedicated program code with which the main control unit of the gymnastic machine is provided;
controlling the gymnastic machine, by the main control unit of the gymnastic machine, based on the generated operative command.

19. Method according to claim 12, in the case that the input command is a tactile or a gestural command, the step of generating comprises a step of interpreting, by the main control unit of the gymnastic machine, the input tactile command received via a program code for recognizing tactile commands inserted via the touchpad, or the gestural command received via a dedicated program code for recognizing gestural commands, said program codes being stored in the memory unit of the gymnastic machine.

20. Method according to claim 17, comprising, in the case that the input command received by the electronic device is the request of at least one physical parameter of the training of the user, a step of providing the electronic device, by the main control unit of the gymnastic machine, through the wireless-type data communication channel, with said at least one required physical parameter, selected among those received by the electronic device.

21. A non-transitory computer readable medium storing thereon computer executable instructions for controlling a gymnastic machine, including instructions for:

forming, by a main control unit of the gymnastic machine, a wireless-type data communication channel with an electronic device wearable by a user;

receiving, by the main control unit of the gymnastic machine, through the wireless-type data communication channel, from said electronic device wearable by the user, an input command provided by the user to the electronic device wearable by the user, wherein said input command provided by the electronic device of the user wearable by the user comprises at least one of a vocal command, a tactile command on the electronic device wearable by the user, or a gestural command optically detected by the electronic device wearable by the user;

generating, by the main control unit of the gymnastic machine, based on the received input command, an operative command of the gymnastic machine; and controlling, by the main control unit of the gymnastic machine, the gymnastic machine based on the generated operative command;

wherein, in the case that the input command is a vocal command, the step of generating comprises a step of interpreting, by the main control unit of the gymnastic machine, the input vocal command received via a respective speech recognition program code stored in the memory unit of the gymnastic machine.

22. Method according to claim 12, further comprising a step of providing the electronic device wearable by the user, through the wireless-type data communication channel, by the main control unit of the gymnastic machine, with data representative of the changes of the training parameters of the user on the gymnastic machine.

* * * * *